(12) United States Patent
Duewer

(10) Patent No.: US 9,872,663 B2
(45) Date of Patent: Jan. 23, 2018

(54) METHODS, SYSTEMS, APPARATUSES, AND COMPUTER PROGRAMS FOR REMOVING MARKER ARTIFACT CONTRIBUTION FROM A TOMOSYNTHESIS DATASET

(71) Applicant: Sirona Dental, Inc., Long Island City, NY (US)

(72) Inventor: Fred Duewer, Woodside, NY (US)

(73) Assignee: DENTSPLY SIRONA Inc., York, PA (US)

( * ) Notice: Subject to any disclaimer, the term of this patent is extended or adjusted under 35 U.S.C. 154(b) by 27 days.

(21) Appl. No.: 14/613,618

(22) Filed: Feb. 4, 2015

(65) Prior Publication Data

US 2016/0220212 A1   Aug. 4, 2016

(51) Int. Cl.
| | | |
|---|---|---|
| *G06K 9/00* | (2006.01) | |
| *A61B 6/00* | (2006.01) | |
| *A61B 6/14* | (2006.01) | |
| *A61B 6/02* | (2006.01) | |
| *G06T 5/50* | (2006.01) | |
| *A61B 90/00* | (2016.01) | |
| *G06T 5/00* | (2006.01) | |
| *G06T 7/33* | (2017.01) | |

(52) U.S. Cl.
CPC ............ *A61B 6/5258* (2013.01); *A61B 6/025* (2013.01); *A61B 6/027* (2013.01); *A61B 6/14* (2013.01); *A61B 6/5252* (2013.01); *A61B 6/584* (2013.01); *A61B 90/39* (2016.02); *G06T 5/005* (2013.01); *G06T 5/50* (2013.01); *G06T 7/337* (2017.01); *A61B 6/145* (2013.01); *A61B 2090/3966* (2016.02); *G06T 2207/10116* (2013.01); *G06T 2207/30036* (2013.01); *G06T 2207/30204* (2013.01)

(58) Field of Classification Search
None
See application file for complete search history.

(56) References Cited

U.S. PATENT DOCUMENTS

| | | | | |
|---|---|---|---|---|
| 6,549,607 | B1 * | 4/2003 | Webber | G01N 23/046 378/21 |
| 2005/0226369 | A1 * | 10/2005 | Martin | A61B 6/025 378/22 |
| 2008/0242968 | A1 * | 10/2008 | Claus | A61B 6/032 600/407 |
| 2009/0268865 | A1 * | 10/2009 | Ren | A61B 6/0414 378/37 |

* cited by examiner

*Primary Examiner* — Tahmina Ansari
(74) *Attorney, Agent, or Firm* — Leana Levin; Douglas J. Hura; David A. Zdurne

(57) ABSTRACT

Method, system, apparatus, and computer program products for removing marker artifacts from a tomosynthesis dataset. In the method, a first plurality of projection images are acquired by tomosynthesis x-ray imaging, the first plurality of projection images containing at least one imaged representation of at least one alignment marker. In one aspect, the imaged representation of the at least one alignment marker on the first plurality of projection images is minimized to generate a second plurality of projection images. In another aspect, a plurality of tomographic images are reconstructed from the second plurality of projection images.

23 Claims, 11 Drawing Sheets

METHODS, SYSTEMS, APPARATUSES, AND COMPUTER PROGRAMS FOR REMOVING MARKER ARTIFACT CONTRIBUTION FROM A TOMOSYNTHESIS DATASET

BACKGROUND

Field

The present application relates generally to obtaining tomographic images in a dental environment, and, more particularly, to methods, systems, apparatuses, and computer programs for removing artifacts from a tomosynthesis dataset.

Description of Related Art

X-ray radiography can be performed by positioning an x-ray source on one side of an object (e.g., a patient or a portion thereof) and causing the x-ray source to emit x-rays through the object and toward an x-ray detector (e.g., radiographic film, an electronic digital detector, or a photostimulable phosphor plate) located on the other side of the object. As the x-rays pass through the object from the x-ray source, the x-rays are transmitted to varying degrees depending on the composition of the object and the energy of the x-rays, and x-rays arriving at the x-ray detector form a two-dimensional (2D) x-ray image (also known as a radiograph) based on the cumulative x-ray attenuation through the object. Thus, a single radiograph does not provide sufficient depth information about features within an object. Features often appear to overlap in a conventional radiograph, although in the object in three-dimensional (3D) space, the features are separate.

X-ray radiography can be performed in dentistry, and dental x-ray radiography systems typically include an x-ray source suspended from a wall-mounted arm and an intraoral x-ray sensor. Dental x-ray radiography systems are relatively compact and conveniently can be used chair-side to provide guidance during a treatment, such as an endodontic procedure. However, dental x-ray radiography also does not provide depth information concerning a patient's unique internal anatomical features (e.g., the shape of dental root structures), although such depth information often would be useful in diagnosing and treating dental pathologies.

X-ray computed tomography (CT), and more particularly cone beam computed tomography (CBCT), has been used to acquire 3D data about a patient, which includes depth information. Dental CBCT is performed by rotating an x-ray source and an x-ray detector with a large field of view (typically, at least large enough to image a patient's complete jaw) through a scan angle of at least 180° around a patient's head, while the patient is sitting or standing in the machine. The 3D data acquired by CBCT can be presented on a display screen for clinician review as a 3D rendering or as a stack of parallel 2D tomographic image slices, each slice representing a cross-section of the patient's anatomy at a specified depth. However, CBCT machines carry a high cost of ownership, are too large for use in chair-side imaging and expose patients to a relatively high dose of x-rays (due to the large field of view, the at least 180° scan angle, and the penetration of x-rays through the complete jaw).

Tomosynthesis is an emerging imaging modality that provides 3D information about a patient in the form of 2D tomographic image slices reconstructed from projection images taken of the patient with an x-ray source from multiple perspectives within a scan angle smaller than that of CBCT (e.g., ±20°, compared with at least 180° in CBCT). Tomosynthesis systems are commercially available for mammographic imaging. Tomosynthesis as an imaging modality can also be applied to intraoral imaging.

Tomosynthesis image slices are reconstructed by processing the projection images taken in a model of the geometry of the tomosynthesis system (e.g., the relative position and angle of the imaged object in 3D space). Spatial instability in the geometry of the tomosynthesis system and/or the object can result in misaligned projection images that deviate from the aforementioned model, which, in turn, can degrade the quality and spatial resolution of the reconstructed tomosynthesis image slices. For example, spatial instability in intraoral tomosynthesis imaging can arise from motion, whether intentional or unintentional, of the patient, the arm-mounted source, and/or the intraoral detector.

Projection images affected by motion or other spatial instabilities can be aligned prior to reconstruction so as to compensate for such motion or instability. One solution is adapted from CBCT imaging to tomosynthesis imaging, namely, placing radiopaque markers within the field of view of the tomosynthesis imaging system, which create visible guides in the projection images that can facilitate realignment of the projection images. For example, three or more highly attenuating marker particles of a known geometry can be placed within the field of view of the imaging system to allow for simple computation of a sample position for a fixed x-ray source and a fixed detector geometry. However, because the field of view in intraoral tomosynthesis is typically smaller than that of CBCT, it can be difficult to place the radiopaque markers in a location that does not obscure relevant anatomical detail in the projection images. In particular, an intraoral sensor is generally restricted to a usable projection angle of ±45 degrees. Thus, objects are typically significantly blurred along the depth directions. Moreover, because intraoral sensors must be small enough to fit inside a subject's mouth, the radiopaque markers tend to obscure relevant dental anatomy wherever the markers are placed.

Additionally, the high contrast edges of radiopaque markers in the projection images can result in major reconstruction artifacts (e.g., out-of-plane contributions and in-plane ringing) in the tomosynthesis images. For example, in back-projection methods, the use of highly attenuating marker particles can result in image artifacts, which are typically characterized by strong streaking throughout the imaged volume due to large image gradients being back-projected through the volume, as well as dimming of imaged features that are obscured by the marker particles. However, in full-angle tomosynthesis imaging, image artifacts are generally benign because any artifacts generated by the marker particles will typically only obscure a small fraction of the imaged volume.

Another solution is to align the projection images based on inherent details and features of the projection images, which is also known as markerless alignment, in contrast to the above-mentioned technique of using radiopaque markers as artificial alignment landmarks. However, the accuracy of markerless alignment is typically limited by the extent in depth of the image features used for alignment. Certain types of imaged anatomy, such as teeth and trabeculae, may contain large, irregular features that are not conducive to markerless alignment.

SUMMARY

Existing limitations associated with the foregoing, as well as other limitations, can be overcome by a method for removing artifacts from a tomosynthesis dataset, and by systems, apparatuses, and computer programs that operate in accordance with the methods.

According to an example embodiment herein, a method, system, apparatus, and computer program product are provided for removing marker artifacts from a tomosynthesis dataset. In the method, a first plurality of projection images are acquired by tomosynthesis x-ray imaging, the first plurality of projection images containing at least one imaged representation of at least one alignment marker. In one aspect, the imaged representation of the at least one alignment marker on the first plurality of projection images is minimized to generate a second plurality of projection images. In another aspect, a plurality of tomographic images are reconstructed from the second plurality of projection images.

The method can be useful for reliable, artifact-free alignment of projection images, which thereby improves the data quality and spatial resolution of reconstructed tomosynthesis images.

Further features and advantages, as well as the structure and operation of various embodiments herein, are described in detail below with reference to the accompanying drawings.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION OF THE PREFERRED EMBODIMENTS

Figure 1A:
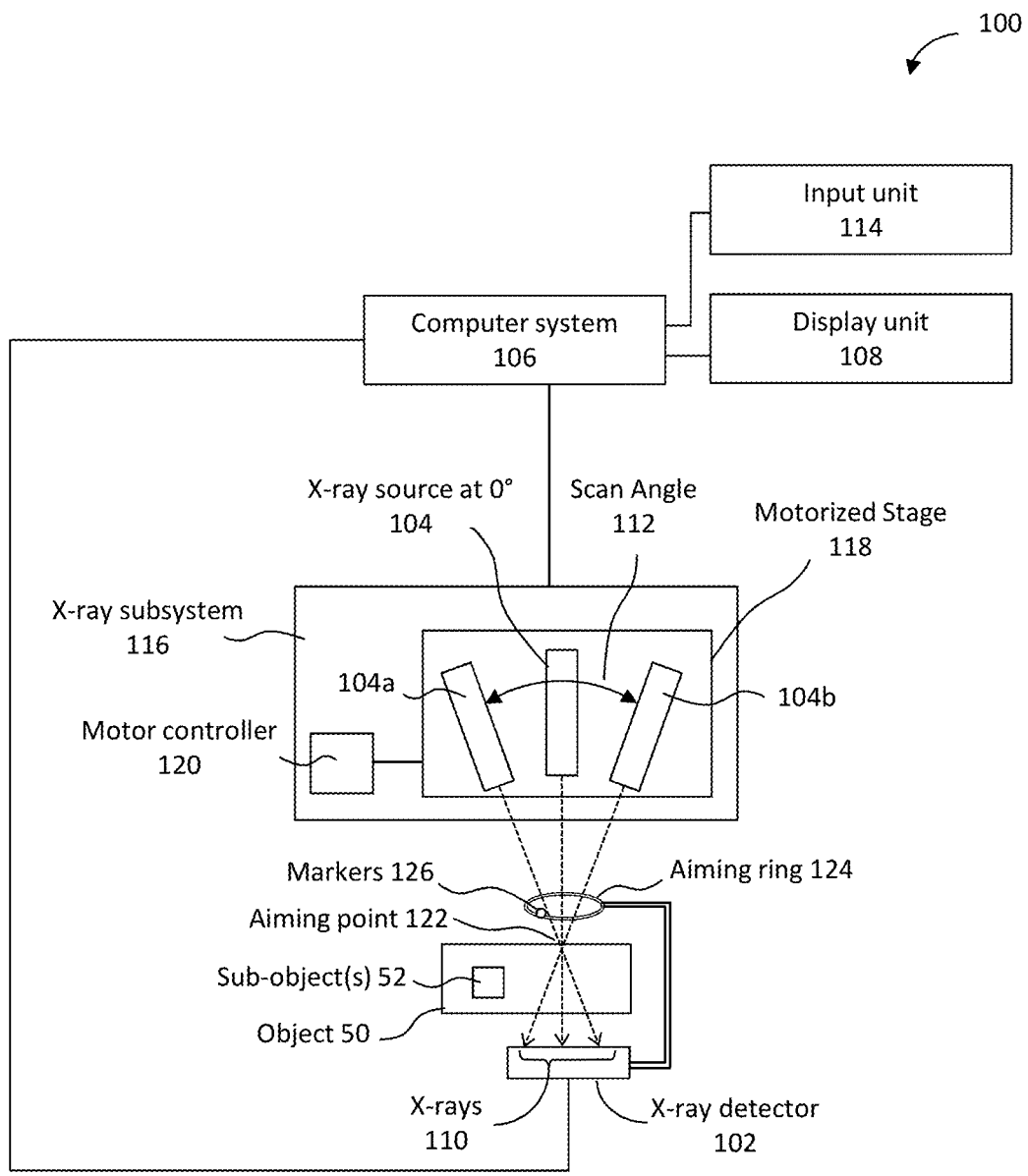
FIG. 1A is a system block diagram of a tomosynthesis system according to one example embodiment herein.

Different ones of the Figures may have at least some reference numerals that are the same in order to identify the same components, although a detailed description of each such component may not be provided below with respect to each Figure.

In accordance with example aspects described herein, methods, systems, apparatuses, and computer programs are provided for removing artifacts from a tomosynthesis dataset.

Tomosynthesis System

FIG. 1A illustrates a block diagram of an intraoral tomosynthesis system 100 for obtaining an intraoral tomosynthesis dataset, and which is constructed and operated in accordance with at least one example embodiment herein. The system 100 can be operated to obtain one or more x-ray images of an object 50 of interest, which may further include one or more sub-object(s) 52. For example, object 50 may be a tooth (or teeth) and surrounding dentition of a patient, and sub-object(s) 52 may be root structures within the tooth.

The system 100 includes an x-ray detector 102 and an x-ray subsystem 116, both of which, including subcomponents thereof, are electrically coupled to a computer system 106. In one example, the x-ray subsystem 116 hangs from a ceiling- or wall-mounted mechanical arm (not shown), so as to be freely positioned relative to an object 50. The x-ray subsystem 116 further includes an x-ray source 104 mounted on a motorized stage 118 and also shows an on-board motor controller 120. The on-board motor controller 120 controls the motion of the motorized stage 118.

The computer system 106 is electrically coupled to a display unit 108 and an input unit 114. The display unit 108 can be an output and/or input user interface.

The x-ray detector 102 is positioned on one side of the object 50 and the receiving surface of the x-ray detector 102 extends in an x-y plane in a Cartesian coordinate system. The x-ray detector 102 can be a small intraoral x-ray sensor that includes, for example, a complementary metal-oxide semiconductor (CMOS) digital detector array of pixels, a charge-coupled device (CCD) digital detector array of pixels, or the like. In an example embodiment herein, the of the x-ray detector 102 varies according to the type of patient to whom object 50 belongs, and more particularly, the x-ray detector 102 may be one of a standard employed in the dental industry. Examples of the standard dental s include a "Size-2" detector, which is approximately 27×37 mm in and is typically used on adult patients, a "Size-1" detector, which is approximately 21×31 mm in and is typically used on patients who are smaller than Size-2 adult patients, and a "Size-0" detector, which is approximately 20×26 mm in and is typically used on pediatric patients. In a further example embodiment herein, each pixel of the x-ray detector 102 has a pixel width of 15 μm, and correspondingly, the Size-2 detector has approximately 4 million pixels in a 1700×2400 pixel array, the Size-1 detector has approximately 2.7 million pixels in a 1300×2000 pixel array, and the Size 0 detector has approximately 1.9 million pixels in a 1200×1600 pixel array. The color resolution of the x-ray detector 102 may be, in one example embodiment herein, a 12-bit grayscale resolution, although this example is not limiting, and other example color resolutions may include an 8-bit grayscale resolution, a 14-bit grayscale resolution, and a 16-bit grayscale resolution.

The x-ray source 104 is positioned on an opposite side of the object 50 from the x-ray detector 102. The x-ray source 104 emits x-rays 110 which pass through object 50 and are detected by the x-ray detector 102. The x-ray source 104 is oriented so as to emit x-rays 110 towards the receiving surface of the x-ray detector 102 in at least the z-axis direction of the Cartesian coordinate system, where the z-axis is orthogonal to the x-y plane associated with the receiving surface of the x-ray detector 102.

In addition to emitting x-rays 110 in the z-axis direction, the x-ray source 104 can also emit x-rays 110 while positioned at each of multiple different locations within a scan angle 112, where a 0° position in the scan angle 112 corresponds to the position for emitting x-rays 110 along the z-axis. In one example embodiment herein, the user initially positions the x-ray subsystem 116, and hence, also the x-ray source 104, to a predetermined starting position relative to the object 50. The computer system 106 then controls the on-board motor controller 120 to move the x-ray source 104 via the motorized stage 118, based on the known starting position, to step through each of the different locations within the scan angle 112. The computer system 106 controls the x-ray source 104 to cause the source 104 to emit x-rays 110 at each of those locations.

The axis of the x-ray source 104 is positioned for each location so that the extension of the source axis substantially intersects at an aiming point 122 close to or on the center of the intraoral sensor in the x-y-z Cartesian coordinate system defined by the detector, as discussed above. The aiming point 122 may be, for example, located close to the detector such that x-rays 110 emitted from the x-ray source 104 positioned at the outer limits of the scan angle 112 are aimed at and do not miss the x-ray detector 102. In FIG. 1A, the 0° position is represented in x-ray source 104, while reference numerals 104a and 104b represent the same x-ray source but in two other example positions within the scan angle 112. The scan angle 112 can be, for example, ±20° from the 0° position, although this example is not limiting.

Figure 1B:
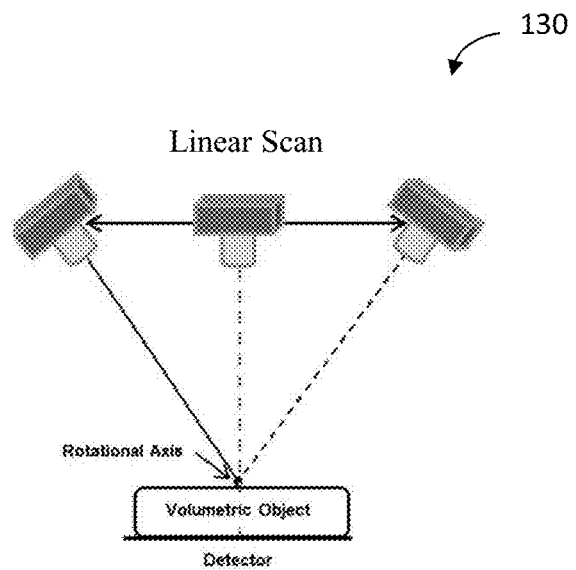
FIG. 1B illustrates an example of a linear scan path used by the tomosynthesis system according to an example embodiment herein.
Figure 1B:
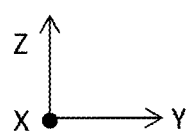
Figure 1C:
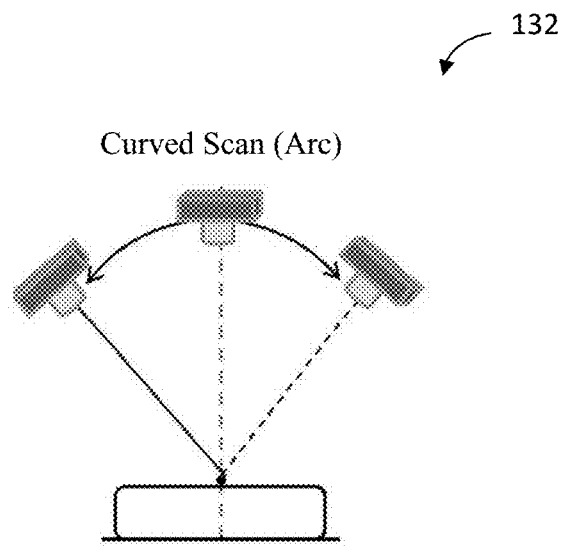
FIG. 1C illustrates an example of a curved scan path used by the tomosynthesis system according to an example embodiment herein.
Figure 1C:
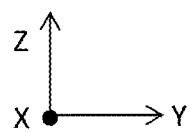
Figure 1D:
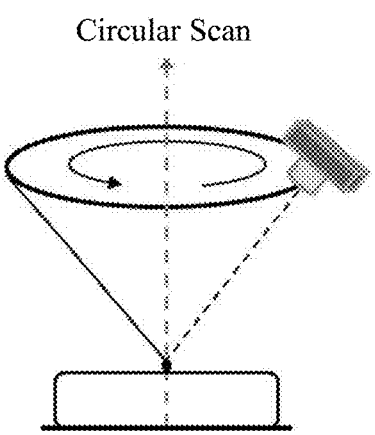
FIG. 1D illustrates an example of a circular scan path used by the tomosynthesis system according to an example embodiment herein.

Additionally, the positioning of x-ray source 104 along the scan angle 112 may form different scan paths, such as, for example, a linear scan 130 shown in FIG. 1B, a curved scan 132 shown in FIG. 1C, or a circular scan 134 shown in FIG. 1D. In the linear scan 130 (FIG. 1B), the x-ray source 104 moves linearly in an x-y plane while emitting x-rays 110 toward the aiming point 122. In the curved scan 132 (FIG. 1C), the x-ray source 104 moves in an arc while emitting x-rays 110 toward the aiming point 122. In the circular scan 134 (FIG. 1D), the x-ray source 104 rotates around the z-axis while emitting x-rays 110 toward the aiming point 122. The scan positions also may be arranged in any particular one or more planes of the Cartesian coordinate system.

As emitted x-rays 110 pass through the object 50, photons of x-rays 110 will be more highly attenuated by high density structures of the object 50, such as calcium-rich teeth and bone, and less attenuated by soft tissues, such as gum and cheek. One or more of the attenuating structures can be sub-object(s) 52. X-rays 110 passing through and attenuated by object 50 (and sub-object(s) 52), are projected onto x-ray detector 102, which converts the x-rays 110 into electrical signals and provides the electrical signals to computer system 106. In one example embodiment, the x-ray detector 102 may be an indirect type of detector (e.g., a scintillator x-ray detector) that first converts x-rays 110 into an optical image and then converts the optical image into the electrical signals, and in another example embodiment, the x-ray detector 102 may be a direct type of detector (e.g., a semiconductor x-ray detector) that converts x-rays 110 directly into electrical signals. The computer system 106 processes the electrical signals to form a two-dimensional projection image of the object 50 in a known manner. In one example embodiment herein, the image of the two-dimensional projection image corresponds to the dimensions and the number of pixels of the x-ray detector 102. Accordingly, pixel values of the two-dimensional projection image represent the cumulative x-ray attenuation through the object 50.

Figure 1E:
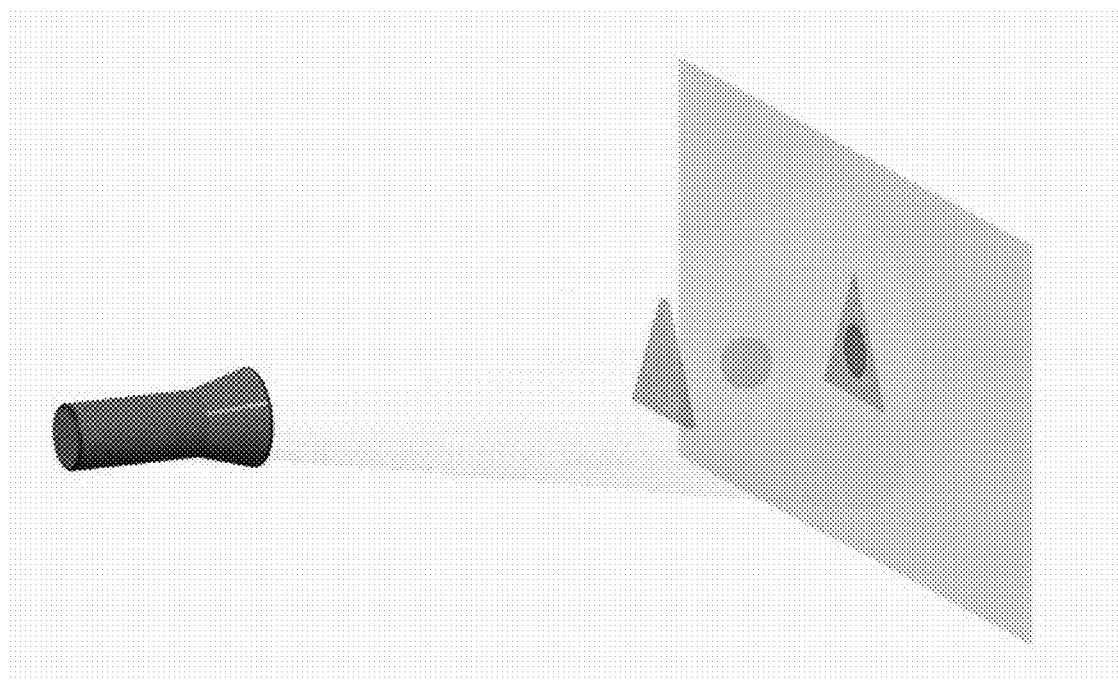
FIG. 1E illustrates an example of shadow casting from an orthogonal projection angle.
Figure 1F:
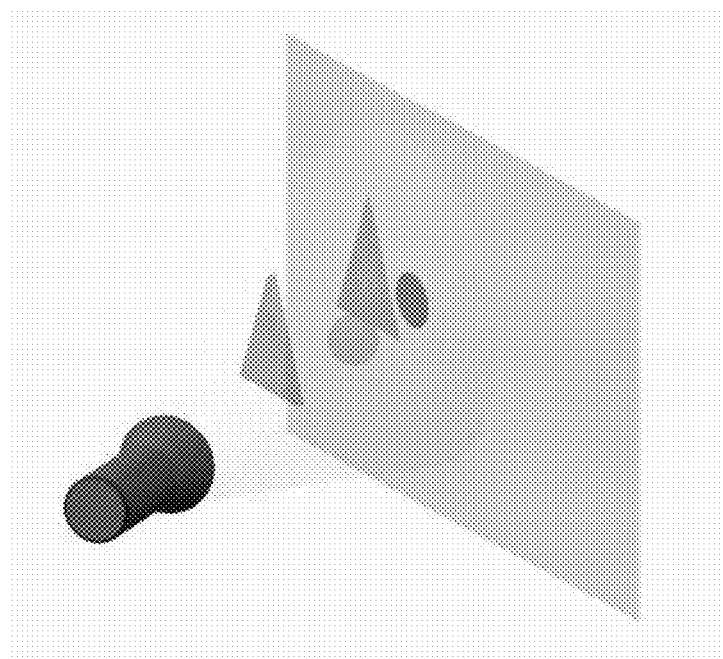
FIG. 1F illustrates an example of shadow casting from a non-orthogonal projection angle and the parallax induced in the image of the objects.

The system 100 can collect a plurality of projection images by first positioning the x-ray source 104 at different angles in scan angle 112, which may include the 0° position, and emitting x-rays 110 at each of those different angles through object 50 towards x-ray detector 102, which, in conjunction with computer system 106, outputs a corresponding projection image for each of the different angles. For example, the plurality of projection images may include a total of fifty-one projections: one orthogonal projection image, obtained when the x-ray source is at the 0° position, and fifty projection images, each obtained when the x-ray source 104 is positioned at different angles within a range of ±20° from the z-axis (corresponding to the scan angle 112). In other example embodiments, the number of projection images may range from twelve to seventy. Because the orthogonal projection image is obtained when the x-ray source is at the 0° position, the orthogonal projection image has the same appearance as a conventional x-ray image. That is, the two-dimensional orthogonal projection image has no depth perception, and one or more sub-object(s) 52 within object 50 may appear overlaid one on top of another in the orthogonal projection image, as represented in FIG. 1E, for example. On the other hand, sub-object(s) 52 at different depths of the z-axis within object 50 undergo varying degrees of parallax when imaged from different angles along the scan angle 112, as represented in FIG. 1E, for example. On the other hand, sub-object(s) 52 at different depths of the z-axis within object 50 undergo varying degrees of parallax when imaged from different angles along the scan angle 112, as represented in FIG. 1F for example.

The x-ray source 104 should be aimed relative to the x-ray sensor 102 such that the full receiving surface of the x-ray sensor 102 is exposed to x-rays 110 emitted by the x-ray source 104 as the x-ray source 104 is swept through the scan angle 112. If the x-ray source 104 is not properly aimed, a part of the x-ray sensor 102 may be left unexposed to x-rays 110 at one or more positions of the x-ray source 104 in the scan angle 112, and the corresponding projection image will appear clear (i.e., white) and devoid of sub-object(s) 52 in the unexposed region. This error is known as a cone cut. To facilitate aiming of the x-ray source 104, an extraoral aiming ring 124 is attached to x-ray sensor 102 to provide a target such that, when x-ray source 104 is at the 0° position, the emitted x-rays 110 are aimed at the center of the x-ray sensor 102 and also are substantially orthogonal to the x-ray sensor 102.

Figure 4A:
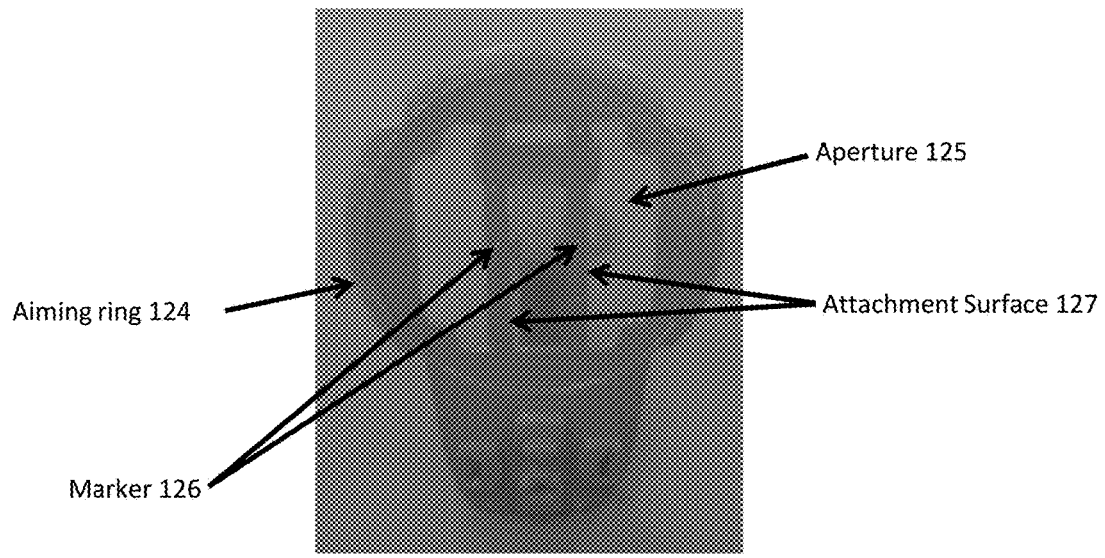
FIG. 4A illustrates a front elevation view of an example aiming ring with markers disposed thereon.

Additionally, the aiming ring 124 includes an aperture 125 and at least one marker 126 disposed within the aperture 125, as illustrated in the example of FIG. 4A. In this embodiment, the at least one marker 126 is provided on at least one attachment surface 127 provided within the aperture 125 of the aiming ring 124. Two attachment surfaces 127 can be provided that each include the at least one marker 126. In addition, as shown in the example of FIG. 4A, the two attachment surfaces 127 can be affixed to opposite sides of the aiming ring 124. As the tomosynthesis system 100 collects the plurality of projection images, as described above, the at least one marker 126 is also imaged by x-rays 110 and thus appears on the plurality of projection images. The presence of the at least one marker 126 on the plurality of projection images facilitates, in a manner described further herein below, alignment of the plurality of projection images prior to reconstruction into a stack of tomosynthesis images.

Figure 4B:
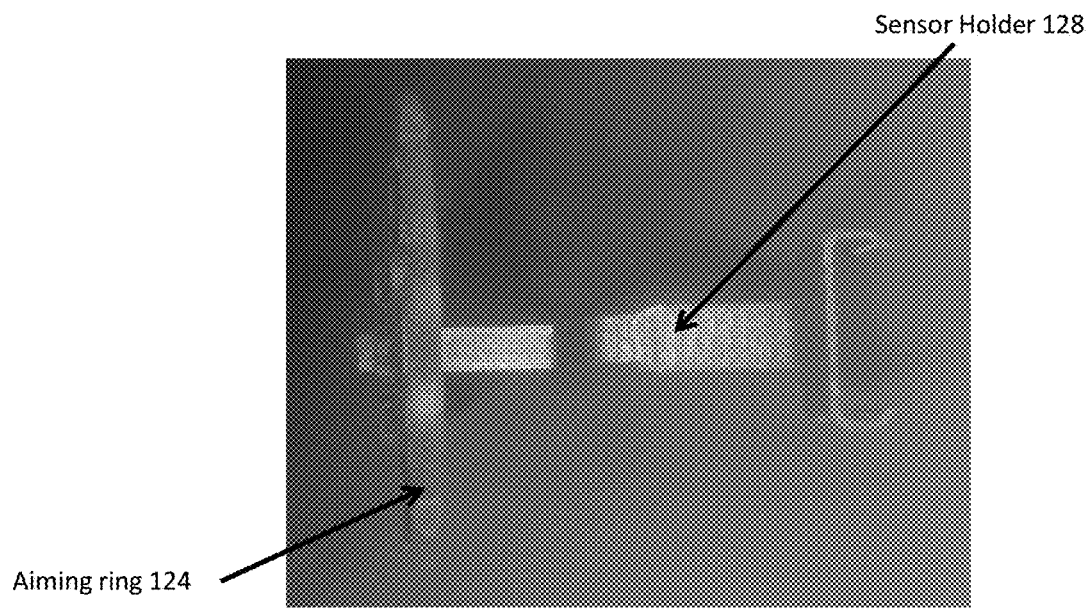
FIG. 4B illustrates a top view of the example aiming ring of FIG. 4A.

In one example embodiment, as shown in FIG. 4B, the aiming ring 124 may be attached to a sensor holder 128 that is adapted to hold the x-ray sensor 102. In another example embodiment herein, the at least one marker 126 can be affixed to the aiming ring 124 approximately two inches from the x-ray sensor 102 by, for example, the positioning of the sensor holder 128. In yet another example embodiment, three separated, non-collinear markers 126 are provided, such that the three markers 126 are visible in each scanned image. By providing at least three visible markers 126 in each scanned image, estimating the system orientation for each image projection is possible. However, given that the markers 126 traverse across the field of view, additional markers may be necessary to ensure that each image projection has a sufficient number of markers. For example, in a further example embodiment herein, thirty markers 126 are affixed to the aiming ring, with at least eight markers 126 visible in the field of view of the x-ray sensor 102.

Additionally, the shape and the x-ray attenuation coefficient of the markers 126 are predetermined, and can be stored in the computer system 106 in one example embodiment herein. For example, in order to locate the markers 126 in a series of image projections that are taken with different system geometries, the markers 126 may be designed to provide sharp edges for a wide angular range. Thus, the shape of the markers 126 should be considered, such that sharp edges are provided. Moreover, the marker attenuation should be sufficiently large, so as to be at least comparable in magnitude with the larger edges of the edges of the image projections upon which the markers are overlaid.

The shape of the marker(s) 126 can be selected from a number of different types, including, for example, spheres (and more particularly, in one example embodiment herein, spheres having a diameter of 100 μm), near-spherical shapes, non-spherical shapes, a periodic structure, and a non-periodic structure. In one example embodiment, spherical or near-spherical particles are used in order to provide the sharp edges needed to effectively locate the markers in a series of image projections, as discussed above. In addition, the of the markers should be considered, given that the use of smaller markers has been found to be beneficial, as it may be possible to minimize artifact creation with the smaller markers, assuming that the markers are localized.

In one example embodiment, a marker 126 is provided that maximizes the ratio of the marker's thickness gradient to the total scanned volume. In addition, in this example embodiment, the marker provided should have a projected shape that does not vary over a broad range of viewing angles. In the case of a spherical marker, the projected shape of the marker does not vary over a broad range of viewing angles; however, the thickness gradient of a spherical marker is low, except at the edges of the sphere. In another example embodiment, a hollow, spherical marker is provided, given that the total volume of the marker's attenuating material remains low, while the thickness gradient remains high. In this example embodiment, the spherical material for the marker should be sufficiently transmissive, to allow for generally unaffected viewing through the center of the spherical marker, and to mimic the x-ray absorption of the bone material being imaged, such that the attenuation contribution of the spherical marker can be effectively removed. Moreover, in this example embodiment, the diameter of the spherical marker should be selected so that the projection of the marker does not overlap with itself on consecutive image projections. In one example embodiment, assuming that the spherical marker is separated from the x-ray sensor 102 by at least 50 mm, and that the tomosynthesis system 100 changes a scan angle 112 by one (1) degree per image projection, a maximum spherical diameter for the marker would be about 0.9 mm. In another example embodiment, the wall thickness of the spherical marker should be of a sufficient thickness in order to provide a good contrast for an edge of the spherical marker when viewed along the edge in a projected image. However, the wall thickness of the spherical marker should also be thin enough to transmit at least 30% of the incoming x-rays 110.

Furthermore, each marker 126 can be constructed to have an x-ray attenuation coefficient that is similar to dental anatomy. For example, the at least one marker 126 can be constructed from steel, aluminum, or any metal or metal alloy that has an energy-dependent x-ray attenuation coefficient similar to bone, and a thinness sufficient to fall within the dynamic range of the tomosynthesis system. By virtue of having a dependence of x-ray attenuation coefficient on x-ray energy similar to bone, a calibrated projection thickness can be calculated for each projection image. Using this calibrated projection thickness, the contribution of the marker 126 can be determined and accurately subtracted, once the marker(s) 126 is located in the image, as discussed in more detail below. In addition, by having a thinness sufficient to fall within the dynamic range of the tomosynthesis system 100 (i.e., the range between the highest and lowest pixel values on an acquired image of dental anatomy), the image contrast and image quality of the region superimposed under the at least one marker 126 is substantially maintained.

In another example embodiment herein, each marker 126 can be constructed as a sphere having a high x-ray attenuating exterior (such as an electroplated radiopaque metal) and a low x-ray attenuating interior (i.e., a radiolucent material). By virtue of the foregoing, the marker 126 is visible on the projection images for the purposes of alignment (owing to the high-x-ray attenuating exterior), but obscures less anatomic detail than a marker 126 that is constructed from a single radiopaque material (owing to the low x-ray attenuating interior), especially through the thickest portion of a sphere-shaped marker 126 (i.e., the center of the sphere). In other words, x-rays 110 passing through a marker 126 having a low x-ray attenuating interior will experience less overall attenuation than x-rays 110 passing through a marker 126 constructed entirely from a radiopaque material.

The computer system 106 aligns the plurality of projection images based on the representation of the markers appearing in the images, minimizes the presence of the markers on the aligned projection images, and processes the plurality of projection images to reconstruct a series of two-dimensional tomosynthesis image slices, also known as a tomosynthesis stack of images, in a manner to be described below. Each image slice is parallel to the plane in which the receiving surface of the x-ray detector 102 extends and at different depths of the z-axis.

One or more image slices of the tomosynthesis stack are provided by the computer system 106 for display to the user on the display unit 108.

Method for Removing Artifacts from a Tomosynthesis Dataset

Figure 3:
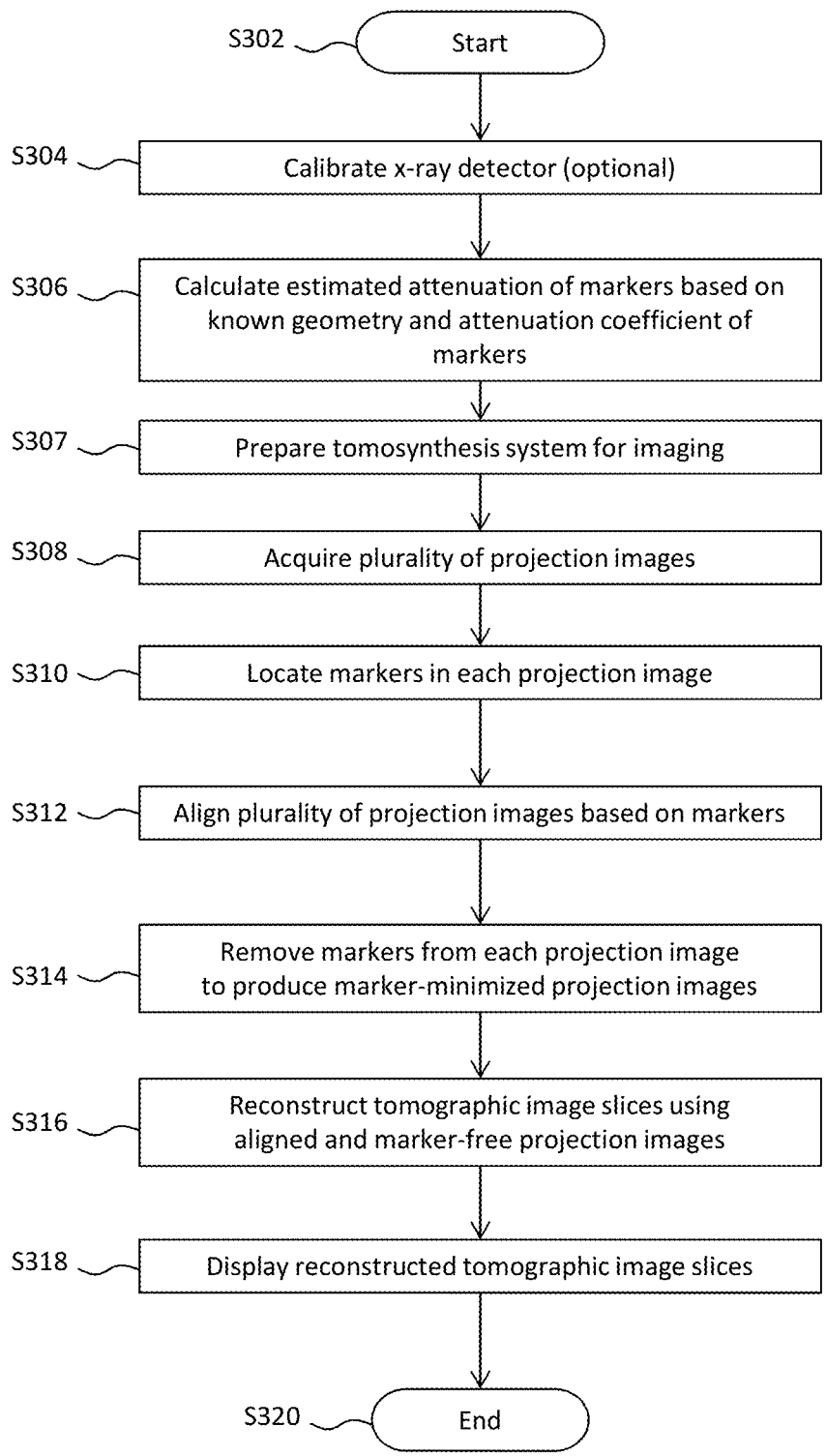
FIG. 3 is a flowchart illustrating a process for acquiring a tomosynthesis dataset and removing marker artifacts therein according to an example embodiment herein.

The intraoral tomosynthesis system 100 will now be further described in conjunction with FIG. 3, which shows a flow diagram of a process according to an example embodiment herein for performing tomosynthesis imaging and removing artifacts from a tomosynthesis dataset.

The process of FIG. 3 starts at Step S302.

In Step S304, a calibration function that can translate measured x-ray attenuation to object thickness and vice versa, and that is specific to the tomosynthesis system 100, is generated. In one example embodiment herein, the calibration function is generated as follows. First, an x-ray phantom (not shown) having a known x-ray attenuation characteristic is placed between the x-ray sensor 102 and the x-ray source 104. For example, for illumination by x-rays of fixed energy, the known x-ray attenuation characteristic of the x-ray phantom will be a cumulative x-ray attenuation through the x-ray phantom, which can be calculated by the Beer-Lambert Law (also known as Beer's Law) from a known thickness of the x-ray phantom and a known x-ray attenuation coefficient of the x-ray phantom. In order to compensate for the broad spectrum of x-rays emitted by a conventional x-ray source, the x-ray attenuation characteristic of the x-ray phantom may be measured. Assuming that the energy flux per kiloelectronvolt of an x-ray source may be modeled as a function F(E) and that the attenuation length of a solid at x-ray energy E may be modeled as a function 1(E), the expected transmission may be calculated by integrating over all energies emitted by the source as:

$$T = \int_0^{E_{max}} F(E) e^{-\frac{t}{l(E)}} dE,$$

where T=is the total transmitted flux through the solid, t is the thickness of the solid, and $E_{max}$ is the maximum x-ray energy emitted by the x-ray source. Given experimental uncertainties (e.g., changes in anode condition with time), estimation of material thickness from x-ray transmission is typically performed using direct measurement of x-ray phantoms materials. After placing the x-ray phantom between the x-ray sensor 102 and the x-ray source 104, an imaging operation is performed by emitting x-rays 110 from the x-ray source 104 toward the x-ray sensor 102, which converts the received x-rays 110 into electrical signals that are processed by the computer system 106 to form a projection image. The calibration function is then generated by correlating the pixel values of the projection image (which represent the cumulative attenuation of the x-rays 110 through the x-ray phantom) with the known x-ray attenuation characteristic of the x-ray phantom.

In an example embodiment herein, Step S304 is performed every time the procedure of FIG. 3 is performed. In at least some other example embodiments herein, Step S304 is optional, that is, Step S304 need not be performed every time the procedure of FIG. 3 is performed, but instead, can be performed periodically (e.g., weekly, monthly, annually, or at other intervals), at irregular intervals, or as necessitated by a change in performance of the x-ray sensor 102 and/or the x-ray source 104 outside of normal operating tolerances (e.g., as defined by a manufacturer's specification).

In Step S306, the computer system 106 uses an inverse of the calibration function to calculate an estimated x-ray attenuation expected to be attributable to an alignment marker 126 appearing in an image acquired by the tomosynthesis system 100, such as in the plurality of projection images acquired in Step S308 described further herein below. In an example embodiment herein, the alignment marker 126 has a known geometry and a known x-ray attenuation coefficient, as described above. Accordingly, the estimated x-ray attenuation and corresponding estimated pixel values are calculated by applying the known geometry and known x-ray attenuation coefficient of the marker 126 to the calibration function generated in Step S304. Assuming that the calibration (Step S304) was performed, the projection images correspond to an equivalent material thickness. Given that the marker geometry and material attenuation properties are known and that the x-ray energy dependence of the marker material is similar to that of the calibration material, the marker model may be calculated as the projection through the solid model of the marker, scaled by the ratio of the attenuation lengths of the marker material to the attenuation length in bone. Assuming that the calibration (Step S304) was not performed, a measure roughly corresponding to thickness may be computed by estimating the negative logarithm of the ratio of the transmitted flux to the transmitted flux when no sample is present. Following that estimate, the marker thickness may be approximated by fitting the region occupied by the marker to a function with spatial dependence identical to the projection through the solid model of the marker and thereby determining a scaling factor. The scaling factor is then combined with the projection through the solid model of the marker to obtain a marker model suitable for subtraction.

In Step S307, the tomosynthesis system 100 is prepared by a user for performing an imaging procedure by manually aiming the x-ray source 104 towards an extraoral aiming ring 124 attached to the x-ray sensor 102, in the manner described above (e.g., aligned so as to avoid cone cut), in one example embodiment herein. The user also verifies that at least one marker 126 disposed on the aiming ring 124 is within the field of view of the x-ray sensor 102.

In Step S308, the intraoral tomosynthesis system 100 acquires a plurality of projection images of object 50 and the at least one marker 126 located within the field of view of the x-ray sensor 102, over a scan angle 112 (which may be predetermined), in the manner described above. For example, the x-ray source 104 is moved by the motorized stage 118 and control circuitry 116 to different positions within the scan angle 112, and the computer system 106 controls the x-ray source 104 to emit x-rays 110 at each position. In one example embodiment herein, x-ray source 104 is scanned while rotating to project x-rays towards the detector at each location from −20° from the z-axis to +20° from the z-axis in evenly distributed increments of 0.8° to provide 51 scan angles, including the 0° position, although this example is not limiting. The x-rays 110 then pass through and are attenuated by the object 50 and the at least one marker 126 before being projected onto the x-ray detector 102. The x-ray detector 102 converts the x-rays 110 into electrical signals (either directly or indirectly, as described above) and provides the electrical signals to the computer system 106. The computer system 106 processes the electrical signals collected at each scan angle position to acquire the plurality of projection images, each image comprising an array of pixels. In particular, the image acquired with the x-ray source 104 at the 0° position is also referred to herein as an orthogonal projection image.

Figure 5:
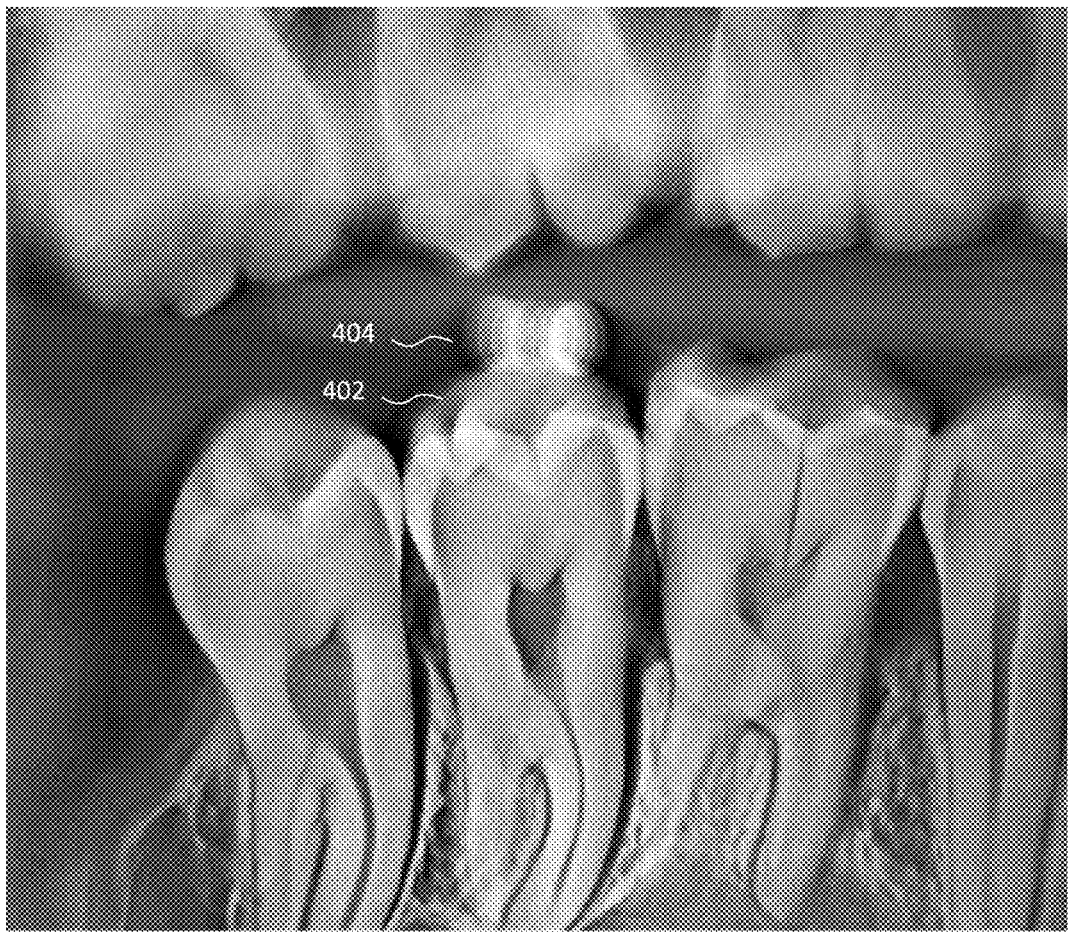
FIG. 5 illustrates an example projection image that includes an image of a marker.
Figure 6:
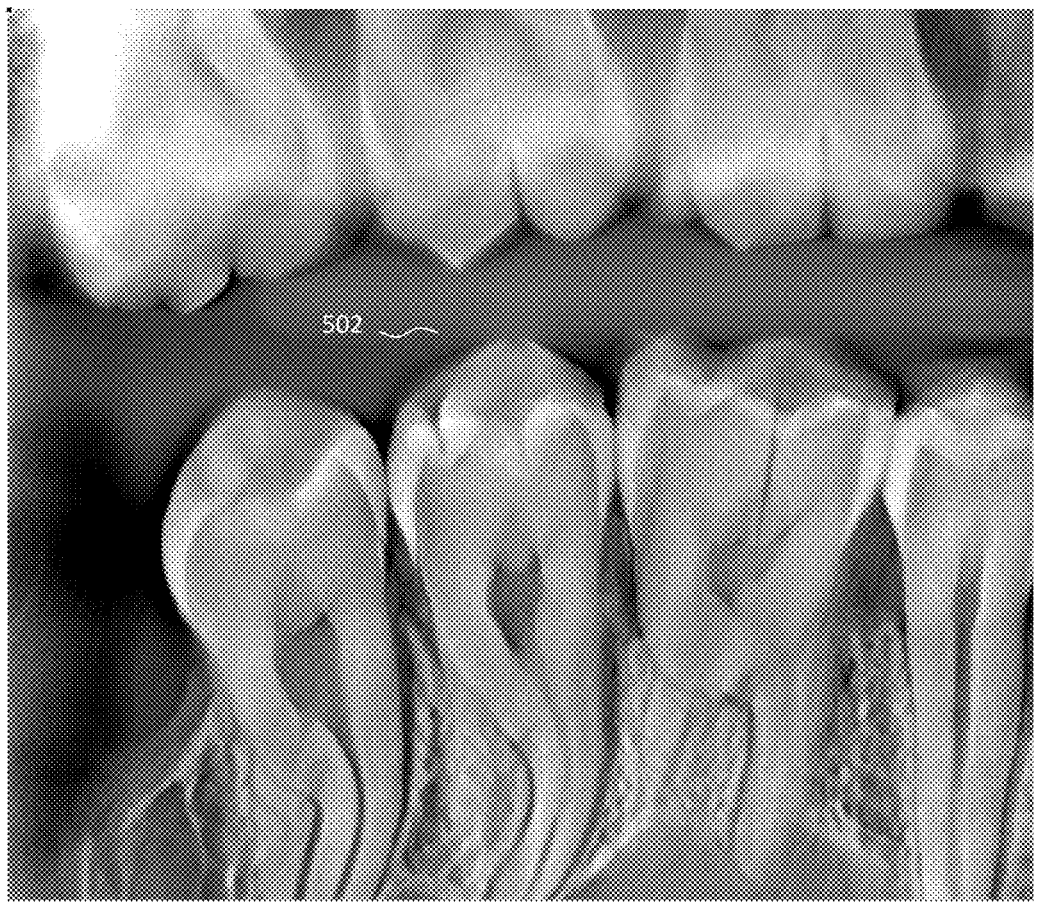
FIG. 6 illustrates the example projection image of FIG. 5 with the marker image removed.

Accordingly, each projection image includes an image representation of the imaged object 50 (e.g., a patient's teeth) and an image representation of the at least one marker 126 (referred to hereafter as a "marker image" for convenience). In other example embodiments, each projection image includes more than one marker image. FIG. 5 illustrates an example projection image acquired according to Step S308 showing teeth 402 and a marker image 404. FIG. 6 illustrates the example projection image of FIG. 5 with the marker image 404 removed, such that area 502 is clear of the marker image 404.

In one example embodiment herein, the color depth of each pixel value of the projection images may be 12-bit grayscale, and the dimensions of the projection images correspond to the standard dental of the x-ray detector 102, as described above. For example, a Size-2 detector may produce projection images that are approximately 1700×2400 pixels in , a Size-1 detector may produce projection images that are approximately 1300×2000 pixels in , and a Size-0 detector may produce projection images that are approximately 1200×1600 pixels in .

In Step S310, the computer system 106 locates the marker images in each of the plurality of projection images. In the example embodiment where the marker 126 is a sphere, the corresponding marker image is circular in shape, and the marker images can be located in a known manner by, for example, a circular Hough transform. In a further example embodiment, a known diameter of the marker 126 can be used to locate the marker using, for example, the circular Hough transform (see e.g., Comparative study of Hough Transform methods for circle finding, Yuen et al, Image and Vision Computing, February 1990, or Generalizing the Hough transform to detect arbitrary shapes, D. H. Ballard, Pattern Recognition (1981)).

In Step S312, the computer system 106 aligns each of the plurality of projection images relative to one another based on the marker images appearing in the plurality of projection images (e.g., marker 404 shown in FIG. 5). In one example embodiment herein, the slices are aligned by performing image registration of corresponding marker images in respective projection images according to a known manner (e.g., linear transformations, which may include rotation, scaling, translation, and the like). In another example embodiment herein, the backprojection matrices used in the later reconstruction process at Step S316 described further herein below can be adjusted to correct for the misalignment of the image slices. Each backprojection matrix is a function of the position of the x-ray source in relation to the detector. The marker positions may be used to estimate the deviation of the x-ray source position from the planned trajectory for a given projection and thereby used to adjust the input parameters used to calculate the backprojection matrix applied to that projection.

After the projection images have been aligned in Step S312, Step S314 is performed to remove or at least substantially minimize the marker images from the plurality of projection images to generate a plurality of marker-minimized projection images. For example, FIG. 6 illustrates an example of a projection image in which the marker image 404 of the projection image of FIG. 5 has been removed, such that an area 502 is clear of the marker image 404. A reason for removing the marker images is that their presence (and in particular, high contrast edges that can be attributed to the marker images) may contribute to reconstruction artifacts such as out-of-plane contributions and in-plane ringing in the tomosynthesis image slices reconstructed from the plurality of projection images in Step S316, which is described further herein below.

Step S314 can be performed according to different techniques, which will now be described in turn.

In one example embodiment herein, Step S314 is performed by subtracting the estimated marker x-ray attenuation calculated in Step 306 from each of the marker images located in Step S310. Because the pixel values of a marker image represent a cumulative attenuation of x-rays through a corresponding marker 126 and through any portion of object 50 in the path of those x-rays, subtracting the estimated marker x-ray attenuation from the projection images leaves, as a remainder, the x-ray attenuation that is primarily attributable to the object 50. Accordingly, by virtue of utilizing a subtraction technique in Step S314, image information about the object 50 (e.g., dental anatomy) that was obscured by the marker images can be revealed. In this example embodiment, the marker 126 must first be located in the scanned image(s), such that the contribution of the marker 126 to the x-ray attenuation in the image content can be removed. In one example embodiment, in which a spherical marker is used, the center of the spherical marker will have a high attenuation contribution, but a low attenuation gradient. Thus, in this example embodiment, the attenuation contribution of the spherical marker towards the center of the spherical marker can be removed by direct subtraction of a linearized attenuation. Moreover, in this example embodiment, the edges of the spherical marker will also have a high attenuation gradient, and the details of this attenuation gradient will depend on the subpixel displacement of the spherical marker. Accordingly, in this embodiment, exact removal of the attenuation gradient contributed by the edges of the spherical particle can be challenging.

In another example embodiment herein, Step S314 is performed by an in-painting technique (instead of the above-described subtraction technique), which defines, for each marker image located in Step S310, a region slightly larger than the marker image and assigns new pixel values to the projection images in those regions. Using the in-painting technique, missing or damaged portions of projection images can be reconstructed. The in-painting technique is computationally simpler than the subtraction technique, but it typically does not preserve image information about the object 50 that was obscured by the marker images. Many different in-painting techniques are possible, including, for example, textural in-painting, interpolating techniques, curvature-based in-painting, or landmark-based in-painting. In one example embodiment, a textural in-painting technique is used. Such a technique is appropriate for qualitative imaging where the esthetic quality of the reconstructed portion of the projection image is of primary importance. For example, in CBCT imaging, in-painting techniques that result in a smooth match between an obscured portion of a projection image and the surrounding portions are preferred. Thus, a textural in-painting might be preferred in this type of example embodiment. In another example embodiment, an in-painting technique is utilized that interpolates inwardly from a specified boundary in a projection image using Laplace's equation. This type of interpolating technique has the advantage of generating a smooth region. However, an in-painting technique that uses interpolating has the disadvantage of generating inaccurate results for features with spatial extents that are smaller than the region being reconstructed. In another example embodiment, a curvature-based in-painting technique can be used. A curvature-based in-painting technique can provide good results for simple objects that are partially obscured in a projection image, such as, for example, the edge of a tooth overlaid by a marker particle. In yet another example embodiment, a landmark-based in-painting technique is used. In a landmark-based in-painting technique, additional known image information can be used, such as, for example, other images in a tomosynthesis series, in order to estimate data missing from a single image being reconstructed.

In another example embodiment herein, after performing either the subtraction technique or the in-painting technique in Step S314, further processing may be performed to reduce image artifacts around the perimeter of the marker images.

In Step S316, the computer system 106 processes the plurality of marker-minimized projection images generated in Step S314 using a reconstruction technique in order to reconstruct a series of two-dimensional tomosynthesis image slices (also known as a stack of tomosynthesis image slices) and may also perform deblurring and other image enhancements, as will be described further herein. Each reconstructed image slice is a tomographic section of object 50 comprising an array of pixels, that is, each image slice represents a cross-section of object 50 that is parallel to the x-y plane in which the receiving surface of the x-ray detector 102 extends, has a slice thickness along the z-axis, and is positioned at a different, respective location along the z-axis than other image slices. The slice thickness is a function of the reconstruction technique and aspects of the geometry of the system 100, including, primarily, the scan angle 112. For example, each image slice may have a slice thickness of 0.5 mm by virtue of the geometry of the system 100 and the reconstruction technique. The desired location of each reconstructed image slice along the z-axis is provided as an input to the reconstruction performed in Step S316 either as a pre-programmed parameter in computer system 106 or by user input via input unit 114 and/or display unit 108. By example only, the computer system 106 can be instructed to reconstruct, from the plurality of projection images, a first image slice that is one millimeter (1 mm) away from the surface of x-ray detector 102 along the z-axis, a last image slice being at fifteen millimeters (15 mm) away from the surface of the x-ray detector 102, and image slices between the first image slice and the last image slice at regular increments along the z-axis of two-hundred micrometers (200 μm), for a total of seventy-one image slices.

In one example embodiment, the sample position is fixed relative to the x-ray detector 102. The sample position can be fixed by, for example, using an apparatus that rigidly holds the x-ray detector 102 in position, including, for example, a bite-block that is clamped between the teeth when an intraoral scan is being conducted. In this example embodiment, for a set of projected images $P_i$, each taken with a system projection matrix $O_i$ that maps an imaged volume based on sampling that volume with a known system geometry, a back-projection matrix $B_i$ can be calculated, such that $V_i = B_i P_i$ with $V_i$ being the back-projected volume and $P_i = O_i V_i$. In this example embodiment, if the system geometry can be determined using alignment markers 126, the back-projection matrices can be modified according to the known system geometry, and used to compute back-projected volumes that can then be added together to reconstruct the sampled volume.

Reconstruction of the tomosynthesis image slices in Step S316 may be performed in accordance with any existing or later developed reconstruction technique. In one example embodiment herein, reconstruction of the tomosynthesis image slices in Step S316 utilizes a shift-and-add technique, such as that described in the publication by D. G. Grant, entitled "Tomosynthesis: A Three-Dimensional Radiographic Imaging Technique", *IEEE Transactions on Biomedical Engineering*, Volume 19, 1972, pp. 20-28, and also described in the review publication by J. T. Dobbins et al., entitled "Digital X-ray Tomosynthesis: Current State of the Art and Clinical Potential", *Physics in Medicine and Biology*, Volume 48, 2003, pp. R65-R106 (the J. T. Dobbins et al. publication), which are incorporated by reference herein in their entireties, as if set forth fully herein. The shift-and-add technique utilizes information about the depth of sub-object(s) 52 along the z-axis that is reflected in the parallax captured by the plurality of projection images, as described above. According to this example embodiment, an image slice is reconstructed by first spatially shifting each projection image by an amount that is geometrically related to the distance between the image slice and the aiming point 122 along the z-axis. The shifted projection images are then averaged together to result in the image slice, where all sub-objects 52 in the plane of the image slice are in focus and sub-objects 52 outside of that plane are out of focus and blurry. This shift-and-add process is repeated for each image slice to be reconstructed. In the case of the image slice corresponding to the x-y plane that includes the aiming point 122, the projection images are averaged together without first shifting because sub-objects 52 are already in focus for that plane.

The foregoing describes a basic shift-and-add reconstruction technique. In one example embodiment herein, a deblurring technique that substantially reduces or removes blurry, out-of-plane sub-objects from an image slice can be performed in conjunction with the reconstruction technique (whether shift-and-add or another technique). Examples of deblurring techniques that can be employed are described in the J. T. Dobbins et al. publication at pp. R81-R90 and include, for example, spatial frequency filtering, ectomography, filtered backprojection, selective plane removal, iterative restoration, and matrix inversion tomosynthesis, each of which may be used in Step S316 to deblur images reconstructed by the shift-and-add reconstruction technique (or another reconstruction technique, if employed).

In another example embodiment herein, Step S316 also can include the computer system 106 performing further automated image enhancements such as, for example, image sharpening, brightness optimization, and/or contrast optimization, on each reconstructed (and deblurred, where deblurring is performed) image slice in a known manner.

In Step 318, one or more image slices from the stack of tomosynthesis image slices generated in Step S316 are displayed on the display unit 108.

The process of FIG. 3 ends at Step S320.

Computer System for Tomosynthesis Imaging

Having described a system 100 for acquiring a tomosynthesis dataset, for aligning images of that dataset, and for removing marker artifacts from that dataset, reference will now be made to FIG. 2, which shows a block diagram of a computer system 200 that may be employed in accordance with at least some of the example embodiments herein. Although various embodiments are described herein in terms of this exemplary computer system 200, after reading this description, it will become apparent to a person skilled in the relevant art(s) how to implement the invention using other computer systems and/or architectures.

Figure 2:
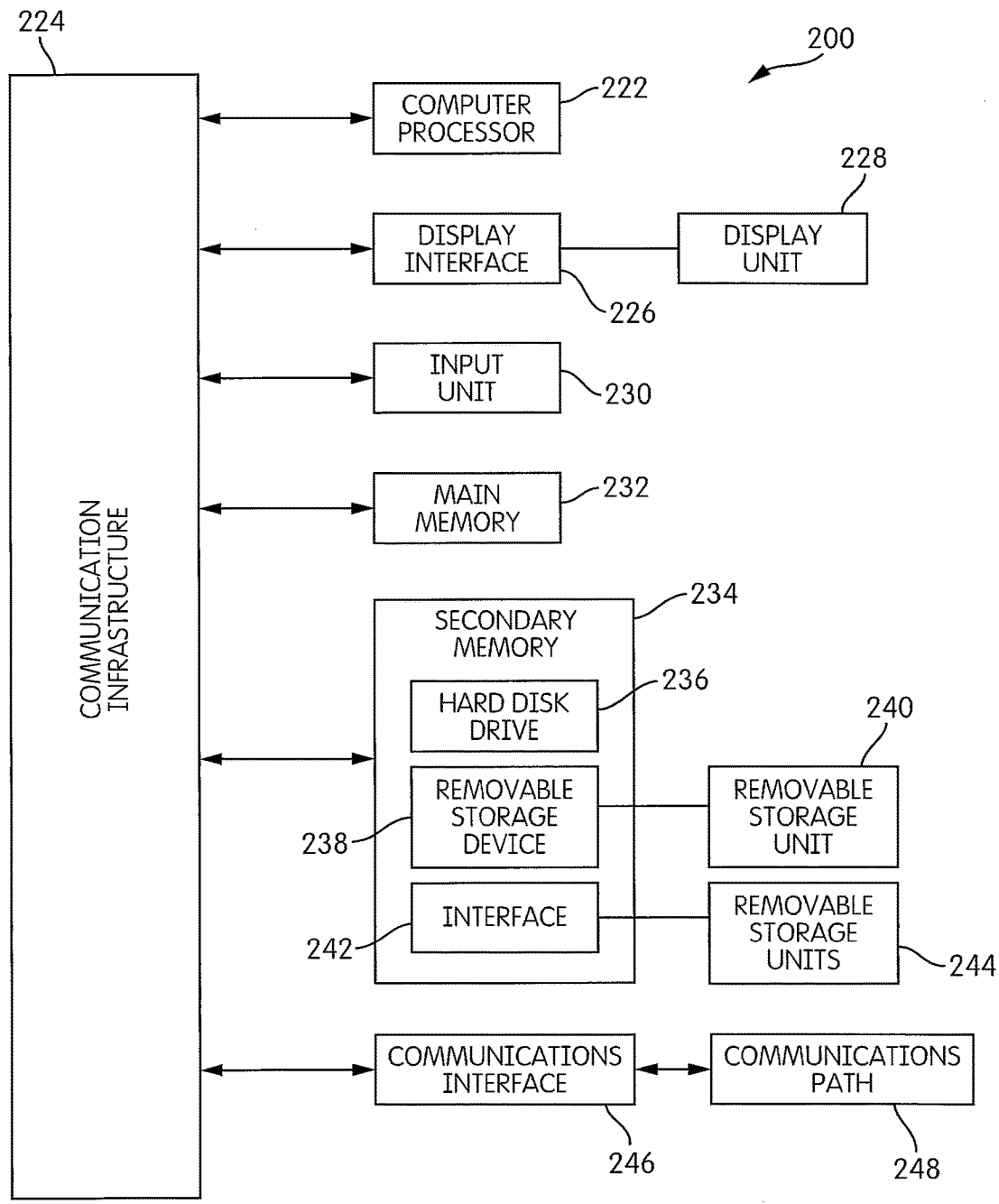
FIG. 2 illustrates a block diagram of an example computer system of the tomosynthesis system shown in FIG. 1A.

FIG. 2 illustrates a block diagram of the computer system 200. In one example embodiment herein, at least some components of the computer system 200 (such as all those components, or all besides component 228) can form or be included in the computer system 106 shown in FIG. 1A. The computer system 200 includes at least one computer processor 222 (also referred to as a "controller"). The computer processor 222 may include, for example, a central processing unit, a multiple processing unit, an application-specific integrated circuit ("ASIC"), a field programmable gate array ("FPGA"), or the like. The processor 222 is connected to a communication infrastructure 224 (e.g., a communications bus, a cross-over bar device, or a network).

The computer system 200 also includes a display interface (or other output interface) 226 that forwards video graphics, text, and other data from the communication infrastructure 224 (or from a frame buffer (not shown)) for display on a display unit 228 (which, in one example embodiment, can form or be included in the display unit 108). For example, the display interface 226 can include a video card with a graphics processing unit.

The computer system 200 also includes an input unit 230 that can be used by a user of the computer system 200 to send information to the computer processor 222. In one example embodiment herein, the input unit 230 can form or be included in the input unit 114. For example, the input unit 230 can include a keyboard device and/or a mouse device or other input device. In one example, the display unit 228, the input unit 230, and the computer processor 222 can collectively form a user interface.

In an example embodiment that includes a touch screen, for example, the input unit 230 and the display unit 228 can be combined, or represent a same user interface. In such an embodiment, a user touching the display unit 228 can cause corresponding signals to be sent from the display unit 228 to the display interface 226, which can forward those signals to a processor such as processor 222, for example.

In addition, the computer system 200 includes a main memory 232, which preferably is a random access memory ("RAM"), and also may include a secondary memory 234. The secondary memory 234 can include, for example, a hard disk drive 236 and/or a removable-storage drive 238 (e.g., a floppy disk drive, a magnetic tape drive, an optical disk drive, a flash memory drive, and the like). The removable-storage drive 238 reads from and/or writes to a removable storage unit 240 in a well-known manner. The removable storage unit 240 may be, for example, a floppy disk, a magnetic tape, an optical disk, a flash memory device, and the like, which is written to and read from by the removable-storage drive 238. The removable storage unit 240 can include a non-transitory computer-readable storage medium storing computer-executable software instructions and/or data.

In alternative embodiments, the secondary memory 234 can include other computer-readable media storing computer-executable programs or other instructions to be loaded into the computer system 200. Such devices can include a removable storage unit 244 and an interface 242 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 244 and interfaces 242 that allow software and data to be transferred from the removable storage unit 244 to other parts of the computer system 200.

The computer system 200 also can include a communications interface 246 that enables software and data to be transferred between the computer system 200 and external devices. Examples of the communications interface 246 include a modem, a network interface (e.g., an Ethernet card or an IEEE 802.11 wireless LAN interface), a communications port (e.g., a Universal Serial Bus ("USB") port or a FireWire®port), a Personal Computer Memory Card International Association ("PCMCIA") interface, and the like. Software and data transferred via the communications interface 246 can be in the form of signals, which can be electronic, electromagnetic, optical or another type of signal that is capable of being transmitted and/or received by the communications interface 246. Signals are provided to the communications interface 246 via a communications path 248 (e.g., a channel). The communications path 248 carries signals and can be implemented using wire or cable, fiber optics, a telephone line, a cellular link, a radio-frequency ("RF") link, or the like. The communications interface 246 may be used to transfer software or data or other information between the computer system 200 and a remote server or cloud-based storage (not shown).

One or more computer programs (also referred to as computer control logic) are stored in the main memory 232 and/or the secondary memory 234. The computer programs also can be received via the communications interface 246. The computer programs include computer-executable instructions which, when executed by the computer processor 222, cause the computer system 200 to perform the procedures as described herein and shown in FIG. 3, for example. Accordingly, the computer programs can control the computer system 106 and other components (e.g., the x-ray detector 102 and the x-ray source 104) of the intraoral tomosynthesis system 100.

In one example embodiment herein, the software can be stored in a non-transitory computer-readable storage medium and loaded into the main memory 232 and/or the secondary memory 234 of the computer system 200 using the removable-storage drive 238, the hard disk drive 236, and/or the communications interface 246. Control logic (software), when executed by the processor 222, causes the computer system 200, and more generally the intraoral tomosynthesis system 100, to perform the procedures described herein. In another example embodiment hardware components such as ASICs, FPGAs, and the like, can be used to carry out the functionality described herein. Implementation of such a hardware arrangement so as to perform the functions described herein will be apparent to persons skilled in the relevant art(s) in view of this description. In view of the foregoing description, it can be appreciated that high quality tomosynthesis image slices can be reconstructed from aligned and substantially marker-free projection images.

As will be appreciated by those of skill in the relevant art(s) in view of this description, the example aspects described herein can be implemented using a single computer or using a computer system that includes multiple computers each programmed with control logic to perform various of the above-described functions.

The various embodiments described above have been presented by way of example and not limitation. It will be apparent to persons skilled in the relevant art(s) that various changes in form and detail can be made therein (e.g., different hardware, communications protocols, and the like) without departing from the spirit and scope of the present invention. Thus, the present invention should not be limited by any of the above-described exemplary embodiments, but should be defined only in accordance with the following claims and their equivalents.

In addition, it should be understood that the attached drawings, which highlight functionality described herein, are presented as illustrative examples. The architecture of the present invention is sufficiently flexible and configurable, such that it can be utilized and navigated in ways other than that shown in the drawings.

Moreover, the example embodiments described herein are not limited to intraoral tomosynthesis imaging. The example embodiments described herein can be used to perform scans of other anatomical regions.

Further, the purpose of the Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way. It is also to be understood that the procedures recited in the claims need not be performed in the order presented.

What is claimed is:

1. A method for removing marker artifacts from a tomosynthesis dataset in a tomosynthesis imaging system comprising:
    positioning at least one alignment marker anywhere within a field of view of the tomosynthesis imaging system;
    acquiring a first plurality of projection images by tomosynthesis x-ray imaging, the first plurality of projection images containing at least one imaged representation of the at least one alignment marker;
    minimizing the imaged representation of the at least one alignment marker on the first plurality of projection images to generate a second plurality of projection images; and
    reconstructing a plurality of tomographic images from the second plurality of projection images
    wherein if the at least one alignment marker is more than one, then a correlation between each alignment marker is not predetermined.

2. The method of claim 1, further comprising locating the imaged representation of the at least one alignment marker on the first plurality of projection images.

3. The method of claim 2, further comprising generating a calibration to convert x-ray attenuation to bone thickness; and
    estimating an estimated representation of the at least one alignment marker based on a known geometry of the at least one alignment marker and the calibration, wherein
    the minimizing includes subtracting the estimated representation of the at least one alignment marker from the imaged representation of the at least one alignment marker.

4. The method of claim 2, wherein the minimizing includes in-painting the imaged representation of the at least one alignment marker with information from an area of the first plurality of projection images surrounding the imaged representation of the at least one alignment marker.

5. The method of claim 1, further comprising aligning the plurality of projection images relative to each other based on the at least one imaged representation of the at least one alignment marker.

6. The method of claim 1, wherein the at least one alignment marker is spherical or near-spherical.

7. The method of claim 1, wherein the at least one alignment marker is a sphere having a radiopaque exterior and a radiolucent interior.

8. The method of claim 1, wherein the at least one alignment marker is provided on an aiming ring.

9. The method of claim 1, wherein at least three alignment markers are provided.

10. The method of claim 9, wherein the at least three alignment markers are non-collinear.

11. A tomosynthesis imaging system for removing marker artifacts from a tomosynthesis dataset, the system comprising at least one processor operable to:
    acquire a first plurality of projection images by tomosynthesis x-ray imaging, the first plurality of projection images containing at least one imaged representation of at least one alignment marker;
    minimize the imaged representation of the at least one alignment marker on the first plurality of projection images to generate a second plurality of projection images; and
    reconstruct a plurality of tomographic images from the second plurality of projection images,
    wherein the at least one alignment marker is positioned anywhere within a field of view of the tomosynthesis imaging system, and
    wherein if the at least one alignment marker is more than one, then a correlation between each alignment marker is not predetermined.

12. The system of claim 11, wherein the processor is further operable to locate the imaged representation of the at least one alignment marker on the first plurality of projection images.

13. The system of claim 12, wherein the processor is further operable to generate a calibration to convert x-ray attenuation to bone thickness, and
    estimate an estimated representation of the at least one alignment marker based on a known geometry of the at least one alignment marker and the calibration,
    wherein to minimize the imaged representation, the processor is operable to subtract the estimated representation of the at least one alignment marker from the imaged representation of the at least one alignment marker.

14. The system of claim 12, wherein, to minimize the imaged representation, the processor is operable to perform in-painting of the imaged representation of the at least one alignment marker with information from an area of the first plurality of projection images surrounding the imaged representation of the at least one alignment marker.

15. The system of claim 11, wherein the processor is further operable to align the plurality of projection images relative to each other based on the at least one imaged representation of the at least one alignment marker.

16. An aiming ring of a tomosynthesis imaging system comprising:
    an aperture; and
    at least one alignment marker disposed within the aperture such that the at least one alignment marker appears anywhere within a field of view of the tomosynthesis imaging system, the at least one alignment marker capable of being imaged in a plurality of projection images by tomosynthesis x-ray imaging, and
    wherein if the at least one alignment marker is more than one, then a correlation between each alignment marker is not predetermined.

17. The aiming ring of claim 16, further comprising an attachment surface provided within the aperture, the attachment surface including the at least one alignment marker.

18. The aiming ring of claim 17, wherein at least two attachment surfaces are provided, each of the attachment surfaces being affixed to opposite sides of the aiming ring, and each of the attachment surfaces including at least one alignment marker.

19. The aiming ring of claim 16, wherein the at least one alignment marker is spherical or near-spherical.

20. The aiming ring of claim 16, wherein the at least one alignment marker is a sphere having a radiopaque exterior and a radiolucent interior.

21. The aiming ring of claim 16, wherein at least three alignment markers are provided.

22. The aiming ring of claim 21, wherein the at least three alignment markers are non-collinear.

23. The aiming ring of claim 21, wherein the at least three alignment markers are non-coplanar.

\* \* \* \* \*